United States Patent [19]

Schmid et al.

[11] Patent Number: 5,304,723
[45] Date of Patent: Apr. 19, 1994

[54] BIOLOGICALLY PURE CULTURE OF MALTOPENTAOSE FORMING AMYLASE PRODUCING ALKALOPHILIC BACTERIA

[75] Inventors: Gerhard Schmid; Anton Candussio, both of Munich; August Bock, Kaltenberg, all of Fed. Rep. of Germany

[73] Assignee: Consortium fur elektrochemische Industrie GmbH, Munich, Fed. Rep. of Germany

[21] Appl. No.: 998,931

[22] Filed: Dec. 29, 1992

Related U.S. Application Data

[62] Division of Ser. No. 706,699, May 29, 1991, Pat. No. 5,204,254.

[30] Foreign Application Priority Data

May 31, 1990 [DE] Fed. Rep. of Germany ........ 4017595

[51] Int. Cl.$^5$ .......................... C12N 1/12; C12N 9/28; C12P 19/14
[52] U.S. Cl. .................................. 435/252.1; 435/99; 435/202; 435/822
[58] Field of Search ...................... 435/72, 95, 99, 101, 435/201, 202, 243, 252.1, 822

[56] References Cited

U.S. PATENT DOCUMENTS 4,039,383 8/1977 Pankratz ............................... 435/99
4,151,041 4/1979 Iwamatsu et al. .................. 435/101
4,591,561 5/1986 Yoshigi et al. ...................... 435/101
5,187,093 2/1993 Kulla et al. ........................ 435/252.1

OTHER PUBLICATIONS

Derwent Abstract, Japanese Pat. No. JP-253786, Sep 20, 1988, Norinsho (Assignee).
Candussio et al, "Biochemical and genetic . . . ", Eur. J. Bioch., vol. 191, pp. 177–185 (1990).
Kimura et al, "Cloning of a gene for maltohexaose . . . ," Appl. Microbio. and Biotech., vol. 27, pp. 372–377 (1988).

Primary Examiner—Douglas W. Robinson
Assistant Examiner—Francisco C. Prats
Attorney, Agent, or Firm—Collard & Roe

[57] ABSTRACT

The alkalophilic bacteria (DSM 5853) possesses a maltopentaose producing amylase. The maltopentaose producing amylase, and its derivatives modified by gene manipulation, can be expressed in E. coli. These amylases facilitate the production of maltopentaose.

1 Claim, 2 Drawing Sheets

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 1:

```
Gln Glu Tyr Arg Glu Leu Asn Gln Leu Glu Asn Lys
 1               5                  10

Pro Phe Ser Trp Asp Asn Ala Asn Val Tyr Phe Val
            15                  20

Leu
25
```

( 2 ) INFORMATION FOR SEQ ID NO: 2:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 2:

```
Trp Asp Asn Ala Asn Val
 1               5
```

( 2 ) INFORMATION FOR SEQ ID NO: 3:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO: 3:

TGGGAYAAYG CNAAYGT                                                      17

(2) INFORMATION FOR SEQ ID NO: 4:

(i) SEQUENCE CHARACTERISTICS:
  (A) LENGTH: 5741 bases
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO: 4:

| | | | | |
|---|---|---|---|---|
| GGTACCGCCT | ATCTCAGTGT | GTGAAAGCTA | TGCATCAAAA | TACCTACTCC | 50 |
| ATGAGCGTTT | CTTCAACACG | AATCTACTTT | ATTTAATATT | ATTCATAACG | 100 |
| AAACATCAGA | AAATATTGTT | ATTACCTAAA | TTCCTTGTTT | TTGTCTTTTA | 150 |
| ATGTTGGTCA | ATGTTCTATG | GTTGTGCTAA | TAAAAATGTT | AACGCTTTCT | 200 |
| CAGGAGGCTA | TATGAGAGGG | GTGATGTCTG | CTAAACAATA | AGGATTCATC | 250 |
| AACACCATGG | TTATAAAAAA | TTAAAGATTG | AAAGGAGGAA | AAGGTA ATG | 299 |
| | | | | Met |
| | | | | 1 |

```
AAG CAA CAG CTT AAT CGC GTG ATA AGT ATC GTA TTA TGT TTA ATT          344
Lys Gln Gln Leu Asn arg Val Ile Ser Ile Val Leu Cys Leu Ile
            5               10                  15

GTC ATG CTC TCG GTG TTT GAA AGT ACT ATT ATG TTA TTA CCA GGT          389
Val Met Leu Ser Val Phe Glu Ser Thr Ile Met Leu Leu Pro Gly
            20              25                  30

TCA GTA GAG GTA AAA GGC CAA GAG TAT CGA GAA CTA AAT CAG CTA          434
Ser Val Glu Val Lys Gly Gln Glu Tyr Arg Glu Leu Asn Gln Leu
            35              40                  45

GAA AAT AAA CCT TTT TCA TGG GAT AAT GCA AAC GTT TAC TTT GTG          479
Glu Asn Lys Pro Phe Ser Trp Asp Asn Ala Asn Val Tyr Phe Val
            50              55                  60

TTA ACC GAT CGT TTT TAC AAT GGA AAT ACA AGT AAT GAT AAT TCT          524
Leu Thr Asp Arg Phe Tyr Asn Gly Asn Thr Ser Asn Asp Asn Ser
            65              70                  75

TAT GGG AGA CCG CAA ATA GAT GCT TGG GGT ACA AAC ATT GGT ACT          569
Tyr Gly Arg Pro Gln Ile Asp Ala Trp Gly Thr Asn Ile Gly Thr
            80              85                  90

TTC CAT GGC GGG GAC ATA AAA GGA TTA ACA AAG AAA TTG GAA GAA          614
Phe His Gly Gly Asp Ile Lys Gly Leu Thr Lys Lys Leu Glu Glu
            95              100                 105

GGT TAC TTT ACA GAC CTA GGT ACA AAT GCC ATA TGG ATA TCT GCT          659
Gly Tyr Phe Thr Asp Leu Gly Thr Asn Ala Ile Trp Ile Ser Ala
            110             115                 120

CCA TGG GAA CAA ATG CAT GGC TGG GTT GGT GGG AAA GAT GGT GAT          704
Pro Trp Glu Gln Met His Gly Trp Val Gly Gly Lys Asp Gly Asp
            125             130                 135

TTT GCT CAC TAT GGC TAT CAT GGT TAC TAT GGA TTA GAT TTT ACG          749
Phe Ala His Tyr Gly Tyr His Gly Tyr Tyr Gly Leu Asp Phe Thr
            140             145                 150

GCT ATG GAT CAG AAT ATG GGT ACA ATT GAT GAA ATG CGT GAA TTT          794
Ala Met Asp Gln Asn Met Gly Thr Ile Asp Glu Met Arg Glu Phe
            155             160                 165

GTT GAC CTT GCA CAT TCA TTA GGC ATT AGA GTT GTT CTC GAC ATT          839
Val Asp Leu Ala His Ser Leu Gly Ile Arg Val Val Leu Asp Ile
            170             175                 180
```

-continued

| | | | | | | | | | | | | | | | |
|---|---|---|---|---|---|---|---|---|---|---|---|---|---|---|---|
| GTT | ATG | AAT | CAC | GTT | GGC | TAT | CCA | ACG | ATC | GTT | GAC | ATG | CAT | GAA | 884 |
| Val | Met | Asn | His | Val | Gly | Tyr | Pro | Thr | Ile | Val | Asp | Met | His | Glu | |
| | | 185 | | | | | 190 | | | | | 195 | | | |
| TTT | GGT | TTT | GGT | GAT | ACT | GGA | GGA | CTT | CCA | AGA | GAT | TGG | ACA | CCT | 929 |
| Phe | Gly | Phe | Gly | Asp | Thr | Gly | Gly | Leu | Pro | Arg | Asp | Trp | Thr | Pro | |
| | | 200 | | | | | 205 | | | | | 210 | | | |
| AAT | CAA | GCA | CAG | GGC | CAA | AAT | TGG | CAT | CAC | CAT | AAT | GAC | ATT | ATG | 974 |
| Asn | Gln | Ala | Gln | Gly | Gln | Asn | Trp | His | Thr | His | Asn | Asp | Ile | Met | |
| | | 215 | | | | | 220 | | | | | 225 | | | |
| AAT | AAA | GAC | AAT | GAA | GCA | GCT | TGG | GCG | AAT | TGG | TGG | GGA | AGT | GAC | 1019 |
| Asn | Lys | Asp | Asn | Glu | Ala | Ala | Trp | Ala | Asn | Trp | Trp | Gly | Ser | Asp | |
| | | 230 | | | | | 235 | | | | | 240 | | | |
| TGG | ATT | CGT | GCC | GAT | GAA | ACA | GCC | GGG | TAT | GAC | AAT | TGT | GGT | GGC | 1064 |
| Trp | Ile | Arg | Ala | Asp | Glu | Thr | Ala | Gly | Tyr | Asp | Asn | Cys | Gly | Gly | |
| | | 245 | | | | | 250 | | | | | 255 | | | |
| AGC | GAA | CAG | ACA | ATG | TGT | ATA | GGG | TTC | TTA | CCA | GAT | ATT | AAA | ACG | 1109 |
| Ser | Glu | Gln | Thr | Met | Cys | Ile | Gly | Phe | Leu | Pro | Asp | Ile | Lys | Thr | |
| | | 260 | | | | | 265 | | | | | 270 | | | |
| GAA | GTA | ACC | ACA | GGT | GTT | GAT | TTA | CCA | CCG | ATA | TTG | AGA | AAC | AAG | 1154 |
| Glu | Val | Thr | Thr | Gly | Val | Asp | Leu | Pro | Pro | Ile | Leu | Arg | Asn | Lys | |
| | | 275 | | | | | 280 | | | | | 285 | | | |
| TGG | AAT | GAT | CAA | GCT | AGT | GGC | TAT | GAA | GAT | TGG | TTT | GTT | CCA | GCA | 1199 |
| Trp | Asn | Asp | Gln | Ala | Ser | Gly | Tyr | Glu | Asp | Trp | Phe | Val | Pro | Ala | |
| | | 290 | | | | | 295 | | | | | 300 | | | |
| GCT | GAA | CCT | TAT | CGT | CAA | GAT | TTA | AAC | ATT | GCT | CCG | AAA | GAT | TAT | 1244 |
| Ala | Glu | Pro | Tyr | Arg | Gln | Asp | Leu | Asn | Ile | Ala | Pro | Lys | Asp | Tyr | |
| | | 305 | | | | | 310 | | | | | 315 | | | |
| TTG | ATC | AAA | TGG | ATT | ACT | TCA | TGG | GTT | GAG | GAA | TTC | GGT | ATT | GAT | 1289 |
| Leu | Ile | Lys | Trp | Ile | Thr | Ser | Trp | Val | Glu | Glu | Phe | Gly | Ile | Asp | |
| | | 320 | | | | | 325 | | | | | 330 | | | |
| GGA | TTC | CGT | GTT | GAT | ACA | GCA | AAG | CAT | GTA | GAG | ATT | GAG | CGA | TGG | 1334 |
| Gly | Phe | Arg | Val | Asp | Thr | Ala | Lys | His | Val | Glu | Ile | Glu | Arg | Trp | |
| | | 335 | | | | | 340 | | | | | 345 | | | |
| GCT | GAA | TTG | AAG | AAT | GAA | GCG | GAA | GTA | GCA | CTT | CAA | ACA | TGG | CGA | 1379 |
| Ala | Glu | Leu | Lys | Asn | Glu | Ala | Glu | Val | Ala | Leu | Gln | Thr | Trp | Arg | |
| | | 350 | | | | | 355 | | | | | 360 | | | |
| GAA | AAT | AAC | CCA | GAT | AAG | CCC | GGT | GCT | AAT | TGG | GAT | GAT | AAT | TTC | 1424 |
| Glu | Asn | Asn | Pro | Asp | Lys | Pro | Gly | Ala | Asn | Trp | Asp | Asp | Asn | Phe | |
| | | 365 | | | | | 370 | | | | | 375 | | | |
| TGG | ATG | ACA | GCA | GAA | GTA | TTT | GGA | CAT | GGT | CTT | GGG | AAA | AGC | GAG | 1469 |
| Trp | Met | Trp | Ala | Glu | Val | Phe | Gly | His | Gly | Leu | Gly | Lys | Ser | Glu | |
| | | 380 | | | | | 385 | | | | | 390 | | | |
| TAT | TTT | GAT | TTT | GGT | TTC | GAT | TCT | GTG | ATT | AAT | TTT | GAA | TTC | CAG | 1514 |
| Tyr | Phe | Asp | Phe | Gly | Phe | Asp | Ser | Val | Ile | Asn | Phe | Glu | Phe | Gln | |
| | | 395 | | | | | 400 | | | | | 405 | | | |
| AAT | GCA | AAC | TTC | AAT | AAT | TTA | GAA | GGT | TTA | TTT | TCT | AGA | TAT | GCA | 1559 |
| Asn | Ala | Asn | Phe | Asn | Asn | Leu | Glu | Gly | Leu | Phe | Ser | Arg | Tyr | Ala | |
| | | 410 | | | | | 415 | | | | | 420 | | | |
| AAT | TCA | ATT | AAC | ACT | GAC | CCT | GAT | TTC | AAC | ATG | TTA | AGT | TAT | GTT | 1604 |
| Asn | Ser | Ile | Asn | Thr | Asp | Pro | Asp | Phe | Asn | Met | Leu | Ser | Tyr | Val | |
| | | 425 | | | | | 430 | | | | | 495 | | | |
| TCA | TCT | CAT | GAT | ACA | AAG | CTT | TAT | AGT | AGA | GAT | GAC | CTT | ATT | CAG | 1649 |
| Ser | Ser | His | Asp | Thr | Lys | Leu | Tyr | Ser | Arg | Asp | Asp | Leu | Ile | Gln | |
| | | 400 | | | | | 445 | | | | | 450 | | | |
| GCA | GGT | ACA | GCA | TTA | CTA | TTA | CTT | CCA | GGT | GGC | GTT | CAA | GTG | TTT | 1694 |
| Ala | Gly | Thr | Ala | Leu | Leu | Leu | Leu | Pro | Gly | Gly | Val | Gln | Val | Phe | |
| | | 455 | | | | | 460 | | | | | 465 | | | |
| TAT | GGC | GAT | GAA | ACA | GCT | CGA | CCA | TTA | GGG | GAT | GGT | GGT | TCT | GAT | 1739 |
| Tyr | Gly | Asp | Gly | Thr | Ala | Arg | Pro | Leu | Gly | Asp | Gly | Gly | Ser | Asp | |
| | | 470 | | | | | 475 | | | | | 480 | | | |
| CCT | GAG | CAA | GGT | ACG | CGT | TCA | TCG | ATG | AAT | TGG | GCT | AAT | ATT | AAT | 1784 |
| Pro | Glu | Gln | Gly | Thr | Arg | Ser | Ser | Met | Asn | Trp | Ala | Asn | Ile | Asn | |

|  |  |  |  |  |  |  |  |  |  |  |  |  |  |  |  |
|---|---|---|---|---|---|---|---|---|---|---|---|---|---|---|---|
| | | | | 485 | | | | | 490 | | | | | 495 | |
| CAG | AAT | GTA | CTC | TCT | CAT | TGG | CAA | AAA | CTT | GGT | CAA | TTC | AGA | AAT | 1829 |
| Gln | Asn | Val | Leu | Ser | His | Trp | Gln | Lys | Leu | Gly | Gln | Phe | Arg | Asn | |
| | | | 500 | | | | | 505 | | | | | 510 | | |
| AAT | CAC | ATA | GCT | ATT | GGT | GCG | GGA | GCG | CAT | CAG | AAG | TTA | TCT | GAT | 1874 |
| Asn | His | Ile | Ala | Ile | Gly | Ala | Gly | Ala | His | Gln | Lys | Leu | Ser | Asp | |
| | | | 515 | | | | | 520 | | | | | 525 | | |
| AGT | CCG | TAT | ACG | TTT | GCG | CGT | ACG | TAT | GAA | TCA | GAC | GAT | ATA | GTT | 1919 |
| Ser | Pro | Tyr | Thr | Phe | Ala | Arg | Thr | Tyr | Glu | Ser | Asp | Asp | Ile | Val | |
| | | | 530 | | | | | 535 | | | | | 540 | | |
| GAT | GAA | GTC | GTC | GTT | GCA | ACT | GGG | GCC | CAA | GGA | ACA | ACA | GCT | GTT | 1964 |
| Asp | Glu | Val | Val | Val | Ala | Thr | Gly | Ala | Gln | Gly | Thr | Thr | Ala | Val | |
| | | | 545 | | | | | 550 | | | | | 555 | | |
| ACT | GTA | GAA | GGT | GTT | TTT | GAA | GAT | GGG | ACA | GTT | GTT | CGA | GAT | GCT | 2009 |
| Thr | Val | Glu | Gly | Val | Phe | Gly | Asp | Gly | Thr | Val | Val | Arg | Asp | Ala | |
| | | | 560 | | | | | 565 | | | | | 570 | | |
| TAT | ACT | GGT | GAT | GAG | ACA | ACA | GTA | ACT | AAA | GGG | ACA | GCA | ACA | TTT | 2054 |
| Tyr | Thr | Gly | Asp | Glu | Thr | Thr | Val | Thr | Lys | Gly | Thr | Ala | Thr | Phr | |
| | | | 575 | | | | | 580 | | | | | 585 | | |
| ACT | GCT | GGA | ACA | CAA | GGT | ATT | ATT | CTA | ATC | GAA | AAT | ACA | GCT | GAG | 2099 |
| Thr | Ala | Gly | Thr | Gln | Gly | Ile | Ile | Leu | Ile | Glu | Asn | Thr | Ala | Gly | |
| | | | 590 | | | | | 595 | | | | | 600 | | |
| CCA | GTT | ACT | AAT | TTG | CCG | ATC | GTT | TCA | GCA | ACA | CCT | GGT | AAT | AGT | 2144 |
| Pro | Val | Thr | Asn | Leu | Pro | Ile | Val | Ser | Ala | Thr | Pro | Gly | Asn | Ser | |
| | | | 605 | | | | | 610 | | | | | 615 | | |
| TCT | TTT | AGG | ACA | GAT | GAC | ATA | ACA | ATC | ACG | CTA | AAT | GTT | GAT | CGA | 2189 |
| Ser | Phe | Arg | Thr | Asp | Asp | Ile | Thr | Ile | Thr | Leu | Asn | Val | Asp | Arg | |
| | | | 620 | | | | | 625 | | | | | 630 | | |
| GCG | GAT | ATG | GGG | AAG | TAT | ACA | CTT | GAT | GGA | AGT | GAT | CCA | GCA | GAT | 2234 |
| Ala | Asp | Met | Gly | Lys | Tyr | Thr | Leu | Asp | Gly | Ser | Asp | Pro | Ala | Asp | |
| | | | 635 | | | | | 640 | | | | | 645 | | |
| GGC | CTA | ACG | TTT | ATG | GAT | GGA | GAA | GAA | ATT | GTC | ATT | GGT | GCT | GAT | 2279 |
| Gly | Leu | Thr | Phe | Met | Asp | Gly | Glu | Glu | Ile | Val | Ile | Gly | Ala | Asp | |
| | | | 650 | | | | | 655 | | | | | 660 | | |
| ATG | GAG | TTT | GAT | GAA | ACA | GCA | ACA | TTG | AGA | CTC | TAT | GCA | GAA | AAT | 2324 |
| Met | Glu | Phe | Asp | Gly | Thr | Ala | Thr | Leu | Arg | leu | Tyr | Ala | Glu | Asn | |
| | | | 665 | | | | | 670 | | | | | 675 | | |
| GAA | AAT | GGC | ATA | AGA | ACA | AGG | AGT | TAC | ACA | TAT | AGG | AAG | GTA | GAT | 2369 |
| Gly | Asn | Gly | Ile | Arg | Thr | Arg | Ser | Tyr | Thr | Tyr | Arg | Lys | Val | Asp | |
| | | | 680 | | | | | 685 | | | | | 690 | | |
| CCA | GAT | GCG | TTA | CTT | GAA | GTA | TAT | TTT | AAG | AAA | CCA | GCG | GAT | TGG | 2414 |
| Pro | Asp | Ala | Leu | Leu | Glu | Val | Tyr | Phe | Lys | Lys | Pro | Ala | Asp | Trp | |
| | | | 695 | | | | | 700 | | | | | 705 | | |
| GGA | ACA | CCA | CAT | ATA | TAT | TAC | TAT | GAT | ACA | TTT | CCA | GAG | GAG | CCG | 2459 |
| Gly | Thr | Pro | His | Ile | Tyr | Tyr | Tyr | Asp | Thr | Phe | Pro | Glu | Glu | Pro | |
| | | | 710 | | | | | 715 | | | | | 720 | | |
| GAA | GTC | ACT | TGG | ACT | ACA | GCT | CCA | GAG | ATG | ACA | TTA | GTA | GAG | GAT | 2504 |
| Glu | Val | Thr | Trp | Thr | Thr | Ala | Pro | Glu | Met | Thr | Leu | Val | Glu | Asp | |
| | | | 725 | | | | | 730 | | | | | 735 | | |
| GAT | TGG | TAT | GTA | TAT | GTT | TTT | GAA | AAT | GCT | GAA | AGT | GCC | AAT | ATA | 2549 |
| Asp | Trp | Tyr | Val | Tyr | Val | Phe | Gly | Asn | Ala | Gly | Ser | Ala | Asn | Ile | |
| | | | 740 | | | | | 745 | | | | | 750 | | |
| ATA | TTT | AAG | GAT | TCT | TCA | GGA | AAA | CAA | ATT | CCA | GGT | CCA | AAT | GAA | 2594 |
| Ile | Phe | Lys | Asp | Ser | Ser | Gly | Lys | Gln | Ile | Pro | Gly | Pro | Asn | Glu | |
| | | | 755 | | | | | 760 | | | | | 765 | | |
| CCA | GGA | TTC | TTC | ATT | GAT | CAG | ATT | GGT | TGG | TAC | GAT | GGC | GTA | AAG | 2639 |
| Pro | Gly | Phe | Phe | Ile | Asp | Gln | Ile | Gly | Trp | Tyr | Asp | Gly | Val | Lys | |
| | | | 770 | | | | | 775 | | | | | 780 | | |
| TGG | CTT | GAT | TCA | GAT | CCT | TTT | GAA | AGG | GAA | CCT | AAA | GAG | CCT | GCG | 2684 |
| Trp | Leu | Asp | Ser | Asp | Pro | Phe | Glu | Arg | Glu | Pro | Lys | Glu | Pro | Ala | |
| | | | 785 | | | | | 790 | | | | | 795 | | |

-continued

| | | | | | | | | | | | | | | | |
|---|---|---|---|---|---|---|---|---|---|---|---|---|---|---|---|
| ACA | ACA | CCT | AAG | AAC | CTA | AGT | GTT | GTT | AAT | GTA | ACT | GAA | ACT | ACT | 2729 |
| Thr | Thr | Pro | Lys 800 | Asn | Leu | Ser | Val 805 | Val | Asn | Val | Thr | Glu | Thr 810 | Thr | |
| GTA | ACA | TTT | GAG | TGG | GAC | CAA | TCT | GAT | GGT | TAT | GTC | GTT | GAA | TAC | 2774 |
| Val | Thr | Phe | Gly 815 | Trp | Asp | Gln | Ser | Asp 820 | Gly | Tyr | Val | Val | Glu 825 | Tyr | |
| GAG | ATT | TTA | CGT | GAT | GAG | GAT | GTT | GTT | GCT | TCA | ACT | ATT | CGT | ACA | 2819 |
| Glu | Ile | Leu | Arg 830 | Asp | Glu | Asp | Val | Val 835 | Ala | Ser | Thr | Ile | Arg 840 | Thr | |
| ACA | TTT | ACG | GAT | GAA | GAC | CTT | AAT | CCA | GAT | ACA | ACC | TAC | ACT | TAT | 2864 |
| Thr | Phe | Thr | Asp 845 | Gly | Asp | Leu | Asn | Pro 850 | Asp | Thr | Thr | Tyr | Thr 855 | Tyr | |
| TCT | GTC | GTA | GCT | GTT | GGA | GAA | GGC | GGG | CAG | AAA | TCC | GCC | CCA | AGT | 2909 |
| Ser | Val | Val | Ala 860 | Val | Gly | Glu | Gly | Gly 865 | Gln | Lys | Ser | Ala | Pro 870 | Ser | |
| GAA | GCG | TTA | AAA | GTG | ACT | ACA | TTA | GAA | GAA | AAT | GAT | GAA | CCT | AAG | 2954 |
| Glu | Ala | Leu | Lys 875 | Val | Thr | Thr | Leu | Glu 880 | Glu | Asn | Asp | Glu | Pro 885 | Lys | |
| GAA | CCG | GCT | GAG | GCG | CCA | GAA | AAT | TTA | CGT | ATA | GCT | GAT | ATA | ACA | 2999 |
| Glu | Pro | Ala | Glu 890 | Ala | Pro | Glu | Asn | Leu 895 | Arg | Ile | Ala | Asp | Ile 900 | Thr | |
| GAT | ACA | ACA | GTT | ACA | ATC | AAC | TGG | AAT | GCA | TCT | AAT | GGT | TAC | GTA | 3044 |
| Asp | Thr | Thr | Val 905 | Thr | Ile | Asn | Trp | Asn 910 | Ala | Ser | Asn | Gly | Tyr 915 | Val | |
| ACA | GGA | TAT | GAG | GTT | CTG | CGT | GAT | GGT | GTG | GTT | ATT | GGC | GAA | ACA | 3089 |
| Thr | Gly | Tyr | Glu 920 | Val | Leu | Arg | Asp | Gly 925 | Val | Val | Ile | Gly | Glu 930 | Thr | |
| ACA | CGG | ACA | ACA | TTC | ATA | GAT | ACT | GGA | TTA | GAT | GCT | GAT | AGG | ACC | 3134 |
| Thr | Arg | Thr | Thr 935 | Phe | Ile | Asp | Thr | Gly 940 | Leu | Asp | Ala | Asp | Arg 945 | Thr | |
| TAT | ACG | TAT | ACG | ATT | GTT | GCT | CTC | GGA | GAT | GGC | GGG | CAA | AAG | TCT | 3179 |
| Tyr | Thr | Tyr | Thr 950 | Ile | Val | Ala | Leu | Gly 955 | Asp | Gly | Gly | Gln | Lys 960 | Ser | |
| GAT | CCG | AGC | GAA | GCG | TTA | GAA | GTA | ACA | ACT | CAA | GAA | AAA | CCA | GAA | 3224 |
| Asp | Pro | Ser | Glu 965 | Ala | Leu | Glu | Val | Thr 970 | Thr | Gln | Glu | Lys | Pro 975 | Glu | |
| GGA | AAT | CTA | GTA | ACA | ATA | TAC | TAT | AAA | AAA | GGC | TTT | GAT | ACC | CCA | 3269 |
| Gly | Asn | Leu | Val 980 | Thr | Ile | Tyr | Tyr | Lys 985 | Lys | Gly | Phe | Asp | Thr 990 | Pro | |
| TAT | ATG | CAT | TAT | CGT | CCG | GAA | GGT | GGA | GAG | TGG | ACG | ATC | GTT | CCA | 3314 |
| Tyr | Met | His | Tyr 995 | Arg | Pro | Glu | Gly | Gly 1000 | Glu | Trp | Thr | Ile | Val 1005 | Pro | |
| GGA | ATT | AGA | ATG | GAA | GAA | TCA | GAA | ATA | GCA | GGC | TAT | AGT | AAG | TTA | 3359 |
| Gly | Ile | Arg | Met 1010 | Glu | Glu | Ser | Glu | Ile 1015 | Ala | Gly | Tyr | Ser | Lys 1020 | Leu | |
| ACC | GTT | GAT | ATT | CGG | GAA | GCA | AGC | AAG | TTG | GAA | GTA | GCC | TTT | AAT | 3404 |
| Thr | Val | Asp | Ile 1025 | Arg | Glu | Ala | Ser | Lys 1030 | leu | Glu | Val | Ala | Phe 1035 | Asn | |
| AAT | GGA | CGT | GGG | GCT | TGG | GAT | AGT | GAT | CAA | GAG | AAT | AAT | TAT | TTA | 3449 |
| Asn | Gly | Arg | Gly 1040 | Ala | Trp | Asp | ser | Asp 1045 | Gln | Glu | Asn | Asn | Tyr 1050 | Leu | |
| TTT | GAG | CCA | GGT | GTT | CAT | ACG | TAC | ATT | CCG | AGT | CAT | GAA | GGA | AGA | 3494 |
| Phe | Glu | Pro | Gly 1055 | Val | His | Thr | Tyr | Ile 1060 | Pro | Ser | His | Glu | Gly 1065 | Arg | |
| GGA | GAG | ATT | ATT | CCA | GGT | AAA | CCA | GGA | GCA | CCA | ATC | GAT | GGT | AAT | |
| Gly | Glu | Ile | Ile 1070 | Pro | Gly | Lys | Pro | Gly 1075 | Ala | Pro | Ile | Asp | Gly 1080 | Asn | |
| AAA | GTG | ACG | ATT | TAC | TAT | CAA | AAT | GGC | TTT | GAT | ACG | CCG | TAT | GTT | 3584 |
| Lys | Val | Thr | Ile 1085 | Tyr | Tyr | Gln | Asn | Gly 1090 | Phe | Asp | Thr | Pro | Tyr 1095 | Val | |
| CAT | TAC | CGC | CCA | GAA | GGC | GGA | AAT | TGG | ACC | AAC | GCC | CCA | GGA | TTA | 3629 |
| His | Tyr | Arg | Pro | Glu | Gly | Gly | Asn | Trp | Thr | Asn | Ala | Pro | Gly | Leu | |

-continued

|  | 1100 |  |  |  | 1105 |  |  |  | 1110 |  |  |  |  |  |
|---|---|---|---|---|---|---|---|---|---|---|---|---|---|---|
| AAA | ATG | GAA | GAT | TCA | GAG | TTT | GCA | AGT | TAT | AGT | AGG | TTA | ACG | CTT | 3674 |
| Lys | Met | Glu | Asp | Ser | Glu | Phe | Ala | Ser | Tyr | Ser | Arg | Leu | Thr | Leu | |
|  |  |  | 1115 |  |  |  |  | 1120 |  |  |  |  | 1125 | | |
| GAT | ATT | GGT | GAA | GCT | AAT | CGT | GCA | GAA | GTG | GCT | TTC | AAT | AAC | GGA | 3719 |
| Asp | Ile | Gly | Glu | Ala | Asn | Arg | Ala | Glu | Val | Ala | Phe | Asn | Asn | Gly | |
|  |  |  | 1130 |  |  |  |  | 1135 |  |  |  |  | 1140 | | |
| CGC | GGC | CTT | TGG | GAT | AGT | GAT | AAT | GAA | AAT | AAT | TAT | TTC | TTC | AAT | 3764 |
| Arg | Gly | Leu | Trp | Asp | Ser | Asp | Asn | Glu | Asn | Asn | Tyr | Phe | Phe | Asn | |
|  |  |  | 1145 |  |  |  |  | 1150 |  |  |  |  | 1155 | | |
| ATT | GGC | GAT | AAC | ACT | TAT | ATA | CCA | GGA | AAA | AAC | GGT | TCA | GCT | GGA | 3809 |
| Ile | Gly | Asp | Asn | Thr | Tyr | Ile | Pro | Gly | Lys | Asn | Gly | Ser | Ala | Gly | |
|  |  |  | 1160 |  |  |  |  | 1165 |  |  |  |  | 1170 | | |
| GAG | ATT | TAT | GGA | GGT | AAG | CCA | AGA | CCA | CCA | TTA | GTA | GGA | AAT | GAA | 3854 |
| Glu | Ile | Tyr | Gly | Gly | Lys | Pro | Arg | Pro | Pro | Leu | Val | Gly | Asn | Glu | |
|  |  |  | 1175 |  |  |  |  | 1180 |  |  |  |  | 1185 | | |
| GTA | ATC | ATT | TAT | TAT | AAA | AAT | GGT | TTT | GAT | ACA | CCG | TAT | GTT | CAT | 3899 |
| Val | Ile | Ile | Tyr | Tyr | Lys | Asn | Gly | Phe | Asp | Thr | Pro | Tyr | Val | His | |
|  |  |  | 1190 |  |  |  |  | 1195 |  |  |  |  | 1200 | | |
| TAT | CGT | CCA | GAA | GGT | GGT | ACG | TGG | ACA | AAT | GCA | CCA | GGA | ATA | AAA | 3944 |
| Tyr | Arg | Pro | Glu | Gly | Gly | Thr | Trp | Thr | Asn | Ala | Pro | Gly | Ile | Lys | |
|  |  |  | 1205 |  |  |  |  | 1210 |  |  |  |  | 1215 | | |
| ATG | GAT | AAG | TCA | GAA | ATA | GCA | GGT | TAC | AGT | AAA | ATA | ACG | CTT | GAT | 3989 |
| Met | Asp | Lys | Ser | Glu | Ile | Ala | Gly | Tyr | Ser | Lys | Ile | Thr | Leu | Asp | |
|  |  |  | 1220 |  |  |  |  | 1225 |  |  |  |  | 1230 | | |
| ATT | GGT | CGC | GCA | GAT | CGA | GTA | GAA | GTA | GCC | TTT | AAT | GAC | GGT | CGT | 4034 |
| Ile | Gly | Arg | Ala | Asp | Arg | Val | Glu | Val | Ala | Phe | Asn | Asp | Gly | Arg | |
|  |  |  | 1235 |  |  |  |  | 1240 |  |  |  |  | 1245 | | |
| GGT | GCA | TGG | GAT | AGT | GAT | AAC | GAA | CGT | AAT | TAT | CTC | TTT | GTA | GTC | 4079 |
| Gly | Ala | Trp | Asp | Ser | Asp | Asn | Glu | Arg | Asn | Tyr | Leu | Phe | Val | Val | |
|  |  |  | 1250 |  |  |  |  | 1255 |  |  |  |  | 1260 | | |
| GGT | AAC | AAT | ACT | TAT | GAA | CCA | GGA | ATT | AAC | GGC | GCA | CCT | GGT | CAG | 4124 |
| Gly | Asn | Asn | Thr | Tyr | Glu | Pro | Gly | Ile | Asn | Gly | Ala | Pro | Gly | Gln | |
|  |  |  | 1265 |  |  |  |  | 1270 |  |  |  |  | 1275 | | |
| GTG | AAA | CAT | GGC | GTG | TTA | CCT | GAT | GAT | GGA | GAA | GAT | CCG | GGA | GAT | 4169 |
| Val | Lys | His | Gly | Val | Leu | Pro | Asp | Asp | Gly | Glu | Asp | Pro | Gly | Asp | |
|  |  |  | 1280 |  |  |  |  | 1285 |  |  |  |  | 1290 | | |
| ATT | GAA | GAC | CCT | GAT | CAT | ACC | TCC | CCT | TCA | AAG | CCG | ACT | GAT | TTA | 4214 |
| Ile | Glu | Asp | Pro | Asp | His | Thr | Ser | Pro | Ser | Lys | Pro | Thr | Asp | Leu | |
|  |  |  | 1295 |  |  |  |  | 1300 |  |  |  |  | 1305 | | |
| ACA | GCA | ATA | GCT | ACT | GCT | CAT | ACT | GTT | TCA | TTA | AGC | TGG | ACA | GCT | 4259 |
| Thr | Ala | Ile | Ala | Thr | Ala | His | Thr | Val | Ser | Leu | Ser | Trp | Thr | Ala | |
|  |  |  | 1310 |  |  |  |  | 1315 |  |  |  |  | 1320 | | |
| TCA | GCA | GAC | GAT | GTA | GAA | GTA | GCT | GGG | TAC | AAA | ATT | TAT | CGA | GAT | 4304 |
| Ser | Ala | Asp | Asp | Val | Glu | Val | Ala | Gly | Tyr | Lys | Ile | Tyr | Arg | Asp | |
|  |  |  | 1325 |  |  |  |  | 1330 |  |  |  |  | 1335 | | |
| GGT | GTG | GAA | ATC | GGT | GTT | ACT | GAA | TCA | ACA | ACT | TAT | ACG | GAT | TCA | 4349 |
| Gly | Val | Glu | Ile | Gly | Val | Thr | Glu | Ser | Thr | Thr | Tyr | Thr | Asp | Ser | |
|  |  |  | 1340 |  |  |  |  | 1345 |  |  |  |  | 1350 | | |
| GGC | TTA | ACG | GCA | GAA | ACA | ACG | TAT | AGC | TAT | ATG | GTA | CAA | GCT | TAT | 4394 |
| Gly | Leu | Thr | Ala | Glu | Thr | Thr | Tyr | Ser | Tyr | Met | Val | Gln | Ala | Tyr | |
|  |  |  | 1355 |  |  |  |  | 1360 |  |  |  |  | 1365 | | |
| GAT | ACT | TCT | AAT | AAT | TTC | TCG | GCA | TTA | AGT | GAT | GAA | CTG | ACA | ATT | 4439 |
| Asp | Thr | Ser | Asn | Asn | Phe | Ser | Ala | Leu | Ser | Asp | Glu | Leu | Thr | Ile | |
|  |  |  | 1370 |  |  |  |  | 1375 |  |  |  |  | 1380 | | |
| GAA | ACC | GCC | GAG | AAA | ACG | GGT | GTT | GAT | CCA | GGA | GGG | GAT | ATG | CCT | 4484 |
| Glu | Thr | Ala | Glu | Lys | Thr | Gly | Val | Asp | Pro | Gly | Gly | Asp | Met | Pro | |
|  |  |  | 1385 |  |  |  |  | 1390 |  |  |  |  | 1395 | | |
| TAT | TCC | ACG | AAT | CCA | TCG | TTT | GGT | AAG | AAG | GTA | ACA | ACG | CCA | ATC | 4529 |
| Tyr | Ser | Thr | Asn | Pro | Ser | Phe | Gly | Lys | Lys | Val | Thr | Thr | Pro | Ile | |
|  |  |  | 1400 |  |  |  |  | 1405 |  |  |  |  | 1410 | | |

| | |
|---|---|
| ACA ATT GAT GGT GTT AAT GAC GGG GAA TGG ACA GAT GAT ATG TTG<br>Thr Ile Asp Gly Val Asn Asp Gly Glu Trp Thr Asp Asp Met Leu<br>　　　　1415　　　　　　　　　1420　　　　　　　　　1425 | 4574 |
| ATT GCA ATT GGT ATG GCT GGT GAC GAC CCA CGT TCG CTC GGG GAC<br>Ile Ala Ile Gly Met Ala Gly Asp Asp Pro Arg Ser Leu Gly Asp<br>　　　　1430　　　　　　　　　1435　　　　　　　　　1440 | 4619 |
| AAT TGG TCT ATG CAT GAA ACA CCA ATG GAC CTT ACT CAC CTA TGG<br>Asn Trp Ser Met His Glu Thr Pro Met Asp Leu Thr His Leu Trp<br>　　　　1445　　　　　　　　　1450　　　　　　　　　1455 | 4664 |
| GGA GCA TGG GAC CAT GAG TAC TTG TAT CTT GCT TGG CAA TAT GTA<br>Gly Ala Trp Asp His Glu Tyr Leu Tyr Leu Ala Trp Gln Tyr Val<br>　　　　1460　　　　　　　　　1465　　　　　　　　　1470 | 4709 |
| GAT GTA ACA GAT ATT ATT GAC CCA GCT AAC GCA GGC TCA TCA GCT<br>Asp Val Thr Asp Ile Ile Asp Pro Ala Asn Ala Gly Ser Ser Ala<br>　　　　1475　　　　　　　　　1480　　　　　　　　　1485 | 4754 |
| GGT ACC ACA ATT AGC CAG ATG GAT ATG CCA CAA ACC ATT GCA ATT<br>Gly Thr Thr Ile Ser Gln Met Asp Met Pro Gln Thr Ile Ala Ile<br>　　　　1490　　　　　　　　　1495　　　　　　　　　1500 | 4799 |
| GAT ACC ATC CCA GAG CAA GGT GCA ACA CAT GAT ATG TGG GGG AAA<br>Asp Thr Ile Pro Glu Gln Gly Ala Thr His Asp Met Trp Gly Lys<br>　　　　1505　　　　　　　　　1510　　　　　　　　　1515 | 4844 |
| AAT GGT GGT GAA TCA CTT TGG GGA GGA CCA GAT TTA CCT GAT TAC<br>Asn Gly Gly Glu Ser Leu Trp Gly Gly Pro Asp Leu Pro Asp Tyr<br>　　　　1520　　　　　　　　　1525　　　　　　　　　1530 | 4889 |
| CAA CTA AAT ATC GCA TCT AAT ATG TTC CAT TCA GGC TAT ATT TCT<br>Gln Leu Asn Ile Ala Ser Asn Met Phe His ser Gly Tyr Ile Ser<br>　　　　1535　　　　　　　　　1540　　　　　　　　　1545 | 4934 |
| AGA GCA GTT GAT GGT GTA TTT CCT GTT GAC GAT GGA GGA ATA AAT<br>Arg Ala Val Asp Gly Val Phe Pro Val Asp Asp Gly Gly Ile Asn<br>　　　　1550　　　　　　　　　1555　　　　　　　　　1560 | 4979 |
| TAT AAA ACG GGT GAG GAA GCA GGA ATT ACA GTA AAG TTT TCT AAA<br>Tyr Lys Thr Gly Glu Glu Ala Gly Ile Thr Val Lys Phe Ser Lys<br>　　　　1565　　　　　　　　　1570　　　　　　　　　1575 | 5024 |
| GGT AAA GGG TAT TCA ACA TTG TGG GGG GTG TTA GAT GCT GAT GAT<br>Gly Lys Gly Tyr Ser Thr Leu Trp Gly Val Leu Asp Ala Asp Asp<br>　　　　1580　　　　　　　　　1585　　　　　　　　　1590 | 5069 |
| GCA GTT GAT CCT AGT AAA CTT GTG AAC TTC ACC GAG CTT GCC CAT<br>Ala Val Asp Pro Ser Lys Leu Val Asn Phe Thr Glu Leu Ala His<br>　　　　1595　　　　　　　　　1600　　　　　　　　　1605 | 5114 |
| GAT TCA ACA CGA GAT ACT TTT TAT GAA GCA AAG ATT CCT TTA GCT<br>Asp Ser Thr Arg Asp Thr Phe Tyr Glu Ala Lys Ile Pro Leu Ala<br>　　　　1610　　　　　　　　　1615　　　　　　　　　1620 | 5159 |
| GCA ATT GGT AAT CCC GAC ATT GAA AAT GAA CGC ATT GGT GTC ATG<br>Ala Ile Gly Asn Pro Asp Ile Glu Asn Glu Arg Ile Gly Val Met<br>　　　　1625　　　　　　　　　1630　　　　　　　　　1635 | 5204 |
| ATT CAT CAA GGT GAA TTT TCG CCG ATG GAC ACG CTA CCG AAT GAC<br>Ile His Gln Gly Glu Phe Ser Pro Met Asp Thr Leu Pro Asn Asp<br>　　　　1640　　　　　　　　　1645　　　　　　　　　1650 | 5249 |
| CCC GCA ACA TCC GAT ACA CCA GGT GTG AGT GAA TCA AAT TCG CCA<br>Pro Ala Thr Ser Asp Thr Pro Gly Val Ser Glu Ser Asn Ser Pro<br>　　　　1655　　　　　　　　　1660　　　　　　　　　1665 | 5294 |
| TTA GAA TGG GAA GAC ATT GAC CTG TTA ACA GTG CCA TTT GCA AGA<br>Leu Glu Trp Glu Asp Ile Asp Leu Leu Thr Val Pro Phe Ala Arg<br>　　　　1670　　　　　　　　　1675　　　　　　　　　1680 | 5339 |
| ATT GGC CAA TAA　　　TTATGAAATA AGCCGGCATG AGTCTATGCT<br>Ile Gly Gln | 5381 |
| GGCTTTTTGT ACGGCTGGCA GTTGCACATG CAGAGACGAC ACTGTGGTGT | 5431 |
| AACAGCTAGA TGACAGTAAA TCATTGGCAT TCCAGATGGT CGGAATAAAA | 5481 |
| GACGGATTTG TGTATATAGT AACTCTATTG ATGAAGTTTT CCCGTTAGTT | 5531 |
| CCATCCTCAG ATTATCAATC ATCAATAATA GGTGGTTTCA TGGATTGCTT | 5581 |

-continued

| | | | | |
|---|---|---|---|---|
| AGGAAATATC | GAGGATGACC | TATTTACTGT | TCACTAAATC | TGATTAGAGT | 5631
| TTATTGGTAT | CAAAAAAGCG | TTATTTCTTC | AAAGCAAGAA | GCAGGCAACT | 5681
| GGGATTATCT | ACATTTCCCA | ATGATATGAA | AAATGCTGTT | AAAAAAGATG | 5731
| GTTGAATATT | | | | | 5741

BIOLOGICALLY PURE CULTURE OF MALTOPENTAOSE FORMING AMYLASE PRODUCING ALKALOPHILIC BACTERIA

This is a divisional of copending application(s) Ser. No. 07/706,699 filed on May 29, 1991 now U.S. Pat. No. 5,204,254.

BACKGROUND OF THE INVENTION

1. Field of the Invention

The present invention relates to a maltopentaose (G5) producing amylases and derivatives thereof.

2. The Prior Art

Apart from glucose (glucoamylases) and maltose (β-amylases), only very few maltooligosaccharides can be obtained directly in sufficient purity by hydrolysis of starch using amylases. On hydrolysis of starch, as a rule, α-amylases produce mixtures of glucose and lower molecular weight maltooligosaccharides (G2-G9). Purification of individual components from such mixtures is elaborate and costly. However, individual α-amylases have sufficiently high product specificity to enable the industrial production of defined oligosaccharides. To date, 3 G5 forming amylases have been disclosed:

(a) *Bacillus licheniformis*: U.S. Pat. No. 4,039,383, issued Aug. 2, 1977; Arch. Biochem. Biophys., 155, 290-298, (1973)

The enzyme from the thermophilic organism *Bacillus licheniformis* has a temperature optimum of 70° C. and is active in a wide pH range of pH 4.0-10.0. Its molecular weight (MW) is 22.5 kDa. The initial products of amylose hydrolysis are long chain maltooligosaccharides (G5-Gn) which are, however, further degraded as the reaction progresses to the main product G5 and, in relatively large amounts, also to G1-G4. U.S. Pat. No. 4,039,383 of Aug. 2, 1977, describes a process for the hydrolysis and solubilization of amylose (a substrate of low solubility in water). The dissolved amylose is then used as substrate for the purified amylase to produce G5. Because of the many byproducts, the mixture of products after the enzyme reaction must be purified by chromatography.

(b) *Bacillus cereus* NY-14: Japanese Patent No. 158,099, of Sep. 13, 1982, Which Corresponds to U.S. Pat. No. 4,591,561, of May 27, 1986; Japanese patent No. 142,330, of Aug. 3, 1983; Agric. Biol. Chem., 49 (12), 3369-3376, (1985) (ABC)

The indicated citation (ABC) describes the purification and characterization of a 55 kDa amylase from *Bacillus cereus* NY-14, which shows maximal activity at pH 6.0 and 55° C. The enzyme cleaves starch initially into the maltooligosaccharides G3-G8. The long chain sugars are then subsequently degraded to G1-G5. Japanese Patent No. 158,099, of Sep. 13, 1982, which corresponds to U.S. Pat. No. 4,591,561, of May 27, 1986, describes the production of G5 by culturing a Bacillus strain (NY-14 in this case) in a medium which contains a substrate (starch, amylose, etc.) which can be cleaved into maltooligosaccharides by enzymes which are produced by the organism used. In this process, defined oligosaccharides are obtained by filtration of the culture broth and subsequent chromatography. Japanese Patent No. 142,330 of Aug. 3, 1983, describes the G5-specific enzyme from *Bacillus cereus* NY-14. There is a contradiction in the description of the enzyme to the description in ABC, because the stated MW of the enzyme is 90 kDa in the patent, but is 55 kDa in the publication.

(c) Pseudomonas sp. KO 8940: Japanese Patent No. 44,069, of Mar. 9, 1984; Japanese Patent No. 44,070 of Mar. 9, 1984; Japanese patent No. 253786-87 (Div ex 44069-84); Appl. Microbiol. Biotechnol., 25, 137-142, (1986); Agric. Biol. Chem., 54 (1), 147-156. (1990)

The authors of the Appl. Microbiol. Biotechnol. describe primarily the Pseudomonas isolate KO 8940 and the conditions necessary for production of a G5-amylase. The most recent publication (Agric. Biol. Chem. 54 (1), 147-156 (1990)) describes the purification and biochemical characterization of probably this G5-amylase. The amylase from the Pseudomonas isolate KO 8940 is, however, not expressly mentioned. The purified enzyme has a high initial G5-forming activity. Shorter hydrolysis products occur only after prolonged incubation times. Japanese Patent No. 253786-87 describes the enzyme from Pseudomonas KO 8940 and its use for producing G5. According to this Japanese patent, the amylase has an optimum temperature of 45° C. to 55° C. and an optimum pH of pH 6.0-7.0. Its MW is 72.5 kDa.

Japanese Patent No. 44,070 of Mar. 9, 1984, discloses the amylase producer Pseudomonas KO 8940.

To obtain maltopentaose using the known enzymes, either elaborately purified enzymes are used, or the maltopentaose is elaborately purified from the culture substrate.

SUMMARY OF THE INVENTION

The present invention relates to a maltopentaose producing amylase (A-180) from the isolate 163-26 (DSM 5853) and to processes for preparing derivatives of this amylase. The invention further relates to DNA constructs encoding derivatives of the amylase from the isolate 163-26 (DSM 5853).

The microorganism alkalophilic isolate 163-26 was deposited under the provisions of the Budapest Treaty at the DSM Deutsche Sammlung Von Mikroorganismen Und Zellkulturen GmbH, having the address of Mascheroder Weg 1 B, D-38124 Braunschweig, Germany, and was given Accession Number DSM 5853. The above-described deposited microorganism will irrevocably, and without restriction or condition, be released to the public as of the issue date of a United States patent granted for the above-identified patent application.

According to the present invention, bacteria, preferably alkalophilic starch-degrading bacteria, are screened in a known manner for their ability to produce maltopentaose from starch.

Bacteria with this property are characterized, and the amylolytic enzyme or enzymes are purified and biochemically characterized.

In order to be able to prepare relatively large amounts of the enzyme in prokaryotes, preferably *E. coli*, the enzyme encoding gene is cloned in a vector, preferably a plasmid, and sequenced in a known manner. The encoding gene is modified by directed mutagenesis in such a way that in suitable prokaryotes, the excretion of large amounts of the modified protein, which is able to function as amylase, is possible.

In order to achieve this, the structural gene in the plasmid is placed under the control of an inducible promoter, preferably under the control of the lactose inducible tac promoter. This allows extensive, controllable overproduction of the amylase. In order to prevent intracellular degradation of the enzyme and to make it possible to use the enzyme without elaborate isolation processes, it is desirable to have efficient secretion of the enzyme into the culture medium.

In order to achieve this, the coding region for the signal peptide of a secretable enzyme, preferably the signal peptide of CGTase from *Klebsiella oxytoca*, is fused, while retaining the reading frame, to the structural gene of the enzyme. It is possible, for example, by comparing the protein sequence with the sequences of known amylases to estimate what are functionally important enzyme domains and what are protein regions inessential to the function and, consequently, to subject the structural gene to further modifications which, while retaining the product specificity, result in an enhanced enzyme excretion into the culture medium or bring about an increased enzyme stability in the culture medium.

Hence, there is no necessity for purification or concentration of the enzyme from the culture supernatant. The culture supernatant can be used directly for maltopentaose production. It is then possible, by a suitable choice of the reaction conditions, to design processes in which the maltopentaose yield is so high that purification of the maltopentaose is unnecessary. With yields of G5 above 90%, it is possible to dispense with further purification of the maltopentaose. The maltopentaose can be obtained straightforwardly from the hydrolysis mixtures, for example, by spray drying.

Maltopentaose, the main product of the hydrolysis of starch by the amylase according to the invention and derivatives thereof, is currently used in three areas.

The main area of use of G5 at present is in medical diagnosis. Several different processes have been described for the use of maltooligosaccharides in one method, specifically maltopentaose, as substrates for the accurate determination of the amylase concentrations in body fluids such as urine or serum.

The G5-dependent processes are distinguished in that a number of enzymes are used in combination with unmodified G5 as substrate for the amylase determination. Either the enzymes are added to prevent interference of the measurement with glucose or oligosaccharides present endogenously in the sample material, or they are used in the enzymatic determination of the products resulting from the G5 hydrolysis.

Example: Japanese Patent No. 98282-85: J. Clin. Chem. Clin. Biochem. 21, 45-52, (1983)

Furthermore, maltopentaose can be used in pharmacology in two other areas:

Because of their low sweetening power, their good solubility, and the low viscosity of the solutions, maltooligosaccharides can be used as carbohydrate sources in liquid alimentation for infants, elderly people, or recovering patients.

Fatty acids can also be made soluble in water by esterification with G5. Since solutions of such esterified fatty acids are stable, they are used as infusion solutions after addition of mineral salts.

Example: Japanese Patent No. 226,610, of Oct. 11, 1985

The examples describe the isolation of a maltopentaose producing amylase according to this prior art document, its DNA sequence, its modification by gene manipulation, and its expression in *E. coli*. Also given are examples of starch conversion using the amylase and its genetically engineered modifications.

BRIEF DESCRIPTION OF THE DRAWINGS

Other objects and features of the present invention will become apparent from the following detailed description considered in connection with the accompanying drawings which discloses two embodiments of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
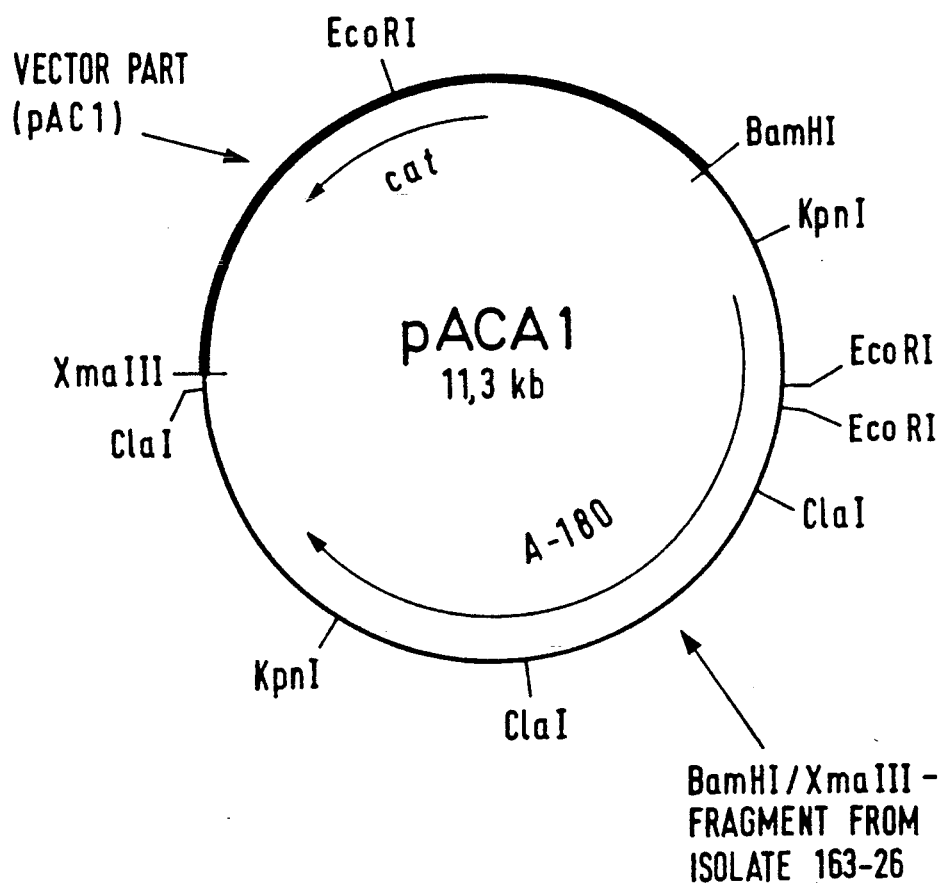
FIG. 1 shows a diagrammatic representation of the plasmid pACA1. A 7.9 kb fragment of chromosomal DNA from the isolate 163-26 was cloned into the BamHI/XmaIII site of the plasmid pAC1 (pACYC184 derivative). The A-180 structural gene contained in the fragment was used to construct the mutants described in the text.

Example 1: Screening for Maltopentaose Producing Alkalophilic Bacteria

Soil samples from various regions of the earth were collected. 0.1–0.2 g of each sample was suspended in 1 ml of sterile physiological saline in sterile vessels. After sedimentation of the coarse fractions, in each case, 0.1 ml was plated on a starch/agar plate (10 g/l soluble starch; 5 g/l peptone; 5 g/l yeast extract; 1 g/l $KH_2PO_4$; 0.2 g/l $MgSO_4 \times 7H_2O$; 10 g/l $Na_2CO_3$; 15 g/l agar; pH 10.4). The agar plates were incubated at 30° C. for 2-3 days. Colonies of starch-degrading bacteria showed a cloudy halo produced by retrogradation of low molecular weight starch molecules. The colonies were isolated and purified twice on starch/agar plates. This was followed by culturing in 2 ml of liquid medium of the above composition. After incubation at 30° C. for 48 hours, the cells were spun down, and the supernatant was assayed for amylase activity. 200 μl of each supernatant were incubated with 200 μl of a 10% starch solution in 20 mM Tris/Cl pH 9.0; 5 mM $CaCl_2$ at 40° C. for 1-5 hours. The enzyme assay was stopped by adding 600 μl of methanol; the supernatant was centrifuged and then analyzed by HPLC. Out of a large number of isolates, only the strain 163-26 showed the G5-producing enzyme activity.

Example 2: Characterization of the Strain

The following features characterize the alkalophilic isolate 163-26:

| Feature | Isolate 163-26 |
| --- | --- |
| Cell Form: | rod-like, sinqle cells, dimers and short chains |
| Cell Size: | 1–1.6 μm × 0.2–0.3 μm |
| Motility: | almost all the cells are motile in the log. growth phase; almost all the cells are non-motile in the stat. growth phase |
| Endospores: | no endospores occur in any growth phase |
| Growth Parameters: | |
| Temperature: | optimal growth between 30° C. and 37° C. |

| Feature | Isolate 163-26 |
| --- | --- |
| pH: | optimal between pH 8.0 and 9.0 |
| NaCl tolerance: | 8% NaCl still tolerated |
| Quinones: | no quinones occur either aerobically or anaerobically |
| Gram Characteristics: | 30%–70% of the cells are Gram-positive in the log. growth phase |
| Fatty Acid Types: | straight-chain and iso-, anteiso-branched fatty acids |
| Murein Type: | A 1 γ |
| GC Content: | 41.5 ± 0.5 mol % |

Example 3: Purification and Characterization of the Amylase A-180

The following is an example of a typical purification procedure:

Isolate 163-26 was cultured in 40 l of M3/1 medium (5 g/l Noredux 150B; 5 g/l peptone from casein; 5 g/l yeast extract; 5 g/l NaCl; 3.5 g/l $Na_2CO_3$; 1 g/l $KH_2PO_4$; 0.2 g/l $MgSO_4$) aerobically at 37° C. for 20 hours. After 20 hours, the culture was rapidly cooled to 4° C. by adding ice. The cells were removed from the culture broth by cross-flow microfiltration in a Millipore filter cassette (pore size 0.2 μm). The proteins in the cell-free culture supernatant were concentrated to a volume of 1 l by ultrafiltration through a Filtron filter cassette (separation limit 10 kDa). The filtrate was brought to 60 percent saturation by the addition of powdered ammonium sulfate. The proteins which were precipitated were collected by centrifugation, dissolved in 50 ml of TC buffer (20 mM Tris/Cl pH 7.2; 5 mM $CaCl_2$), and dialyzed against TC buffer. The amylolytic enzymes in the solution were purified by adsorption to starch. For this purpose, the protein solution after the dialysis was brought to 20% ammonium sulfate saturation, and 3% soluble starch was added. The mixture was stirred at 4° C. for 3 hours and then centrifuged. The precipitate was suspended in half the initial volume of washing buffer (20% saturated with ammonium sulfate, 1M NaCl in TC buffer), stirred at 4° C. for 10 minutes, and centrifuged again. The precipitate resulting from this is suspended in 1 initial volume of elution buffer (3M NaCl; 0.1M maltose in TC buffer) and stirred at 4° C. for 2 hours. The starch is then spun down, and the supernatant is dialyzed against TC buffer. After the dialysis, the proteins in the solution are precipitated by adding ammonium sulfate (60% saturation), dissolved in TC buffer and dialyzed again. The resulting solution now contains only the α-amylases A-60 formed by the isolate 163-26 and the maltopentaose producing amylase A-180. The two enzymes can be separated from one another by gel filtrations on a TSK SW3000G (LKB) molecular sieve column.

Characterization of the Amylase A-180

The MW determination by SDS polyacrylamide gel electrophoresis (PAGE) revealed an MW of about 180 kDa for the amylase A-180. The isoelectric point of the purified enzyme was found to be 4.65 by isoelectric focusing. The kinetics of product formation on hydrolysis of starch revealed an initially very high G5 specificity for the amylase A-I80. A-180 has a biphasic pH optimum at pH values 6.0 and 8.5. Irreversible inactivation of A-180 takes place only at pH values below 5.5 or above 11.0. The optimal temperature for hydrolysis of starch is 55° C., although the enzyme is slightly unstable at this temperature, so that a temperature of 45° C. is used to produce G5. α-Cyclodextrin cannot be hydrolyzed by amylase A-180. This result, together with the finding of high G5 specificity, shows that A-180 is an exo-maltopentaohydrolase.

Example 4: Cloning and Sequencing of the A-180 Structural Gene

Cloning—In order to obtain an A-180 specific probe which can be used to identify the structural gene, initially, the N-terminal amino-acid sequence of the purified amylase A-180 was determined by automated Edman degradation (gas phase sequenator). The amino-acid sequence obtained by the sequencing is: (SEQ ID NO: 1)

It was possible to deduce, by reverse translation, from a part of this sequence (SEQ ID NO: 2) a nucleotide sequence which is 17 bases long and must be present in the A-80 structural gene. The exact sequence of this oligonucleotide is: (SEQ ID No: 3), wherein Y is C or T and N is A, T, C or G.

This oligonucleotide sequence (a 32-fold degenerate 17-mer) was prepared using a DNA synthesizer and radiolabeled with $^{32}p$-α-ATP. Chromosomal DNA of isolate 163-26 was cut with various restriction enzymes, fractionated by electrophoresis in a 0.8% agarose gel, and transferred to a nylon membrane (Southern blot). It was possible to use the radioactive oligonucleotide mixture in hybridization studies to label a 2.7 kB ClaI fragment which codes for the N-terminal region of A-180. The ClaI fragment was isolated, ligated into the vector pBR322 cut with ClaI, and transformed into *E. coli* HB 101. Clones which contained the correct insert were identified by hybridization of their plasmid DNA with the radioactive oligonucleotide mixture. It was possible, using the cloned DNA fragment which was now labeled and was used as hybridization probe, to clone the entire A-180 structural gene.

Sequencing—To determine the nucleotide sequence of the A-180 structural gene, overlapping fragments of the gene were sub-cloned into the plasmid pUC19. The sequence of the subclones was determined by the dideoxy chain termination method using universal or internal sequencing primers. A printout of the complete A-180 nucleotide sequence and the derived amino-acid sequence together with the 5' and 3' flanking regions of the gene is represented below. (SEQ ID NO: 4)

The open reading frame which codes for A-180 comprises 5052 nucleotides, corresponding to 1684 amino acids. The derived MW of 186.5 kDa corresponds to the 180 kDa determined by SDS-PAGE.

Example 5: Mutagenesis of the A-180 Structural Gene

Three mutations were necessary to modify the cloned A-180 structural gene in such a way that massive production, coupled with export and proteolytic stability of the G5-specific amylase, takes place in suitable *E. coli* strains.

In order to obtain massive expression of the A-180 structural gene and, thus, extensive amylase production, which can also be controlled by simple methods (i.e., induction/repression) the A-180 structural gene was placed under the control of a new promoter. For this, the A-180 structural gene was isolated from the plasmid pACA1 (FIG. 1) and cloned downstream of the tac promoter in the polylinker of the expression plasmid pJF118u (Gene 48, 119–131, 1986 1); a derivative of pKK 223 (the latter is obtainable from Pharmacia, Freiburg). This promoter is repressed by the lacI^q gene product (which is likewise encoded on pJF118u) until inducers such as lactose or analogous compounds, for example, IPTG, are added to the medium.

Although this mutation made massive production of A-180 possible, the recombinant gene product was 100% located in the cytoplasm of *E. coli* and was extensively degraded there.

Figure 2:
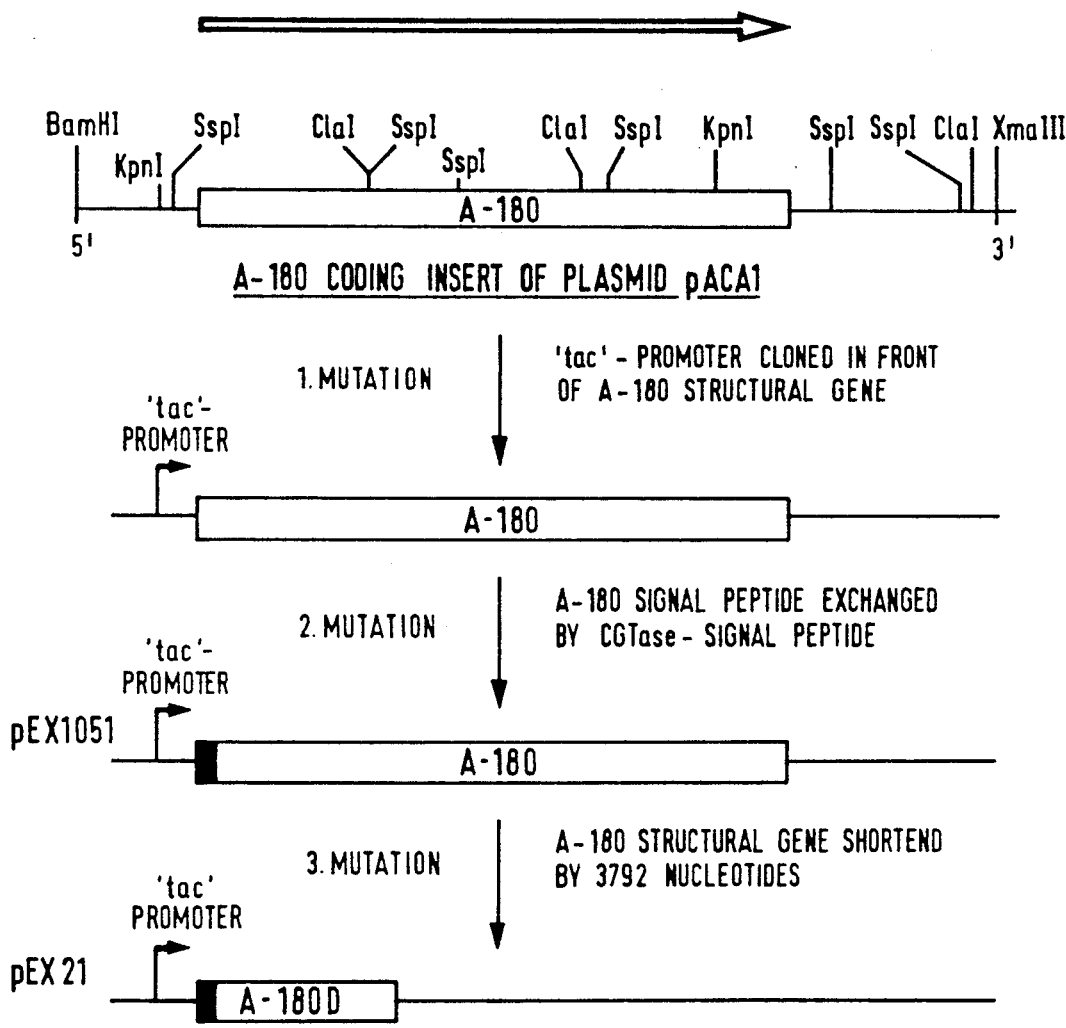
FIG. 2 shows a restriction map of the DNA fragment which was cloned from the isolate 163-26 into the vector pAC1 (pACA1). The diagrammatic representation shows the mutations which resulted in the expression plasmids pEX1051 and pEX21.

In order to achieve export of the produced amylase A-180 into the culture supernatant, the 37 N-terminal amino acids of A-180, which represent the signal peptide necessary for export, were deleted and replaced by the signal peptide of the CGTase from *Klebsiella oxytoca* which is exported in *E. coli* [Gene 47, 269-277, (1986)]. The recombinant plasmid is called pEX1051 (FIG. 2). Expression of the recombinant gene continued via the "tac" promoter. Replacement of the signal peptide resulted in no alteration in the export behavior of A-180. The massively produced enzyme continues to be located in the cytoplasm and is extensively degraded. The G5 specificity is retained, despite the signal peptide exchange.

The third mutation comprised truncating the A-180 structural gene by 3792 nucleotides at the 3' end. The deletion of these nucleotides and the integration of a stop triplet let in their place truncates the amylase on the C terminus by exactly 1264 amino acids [plasmid pEX21 (FIG. 2)]. The remaining amylase residue is, like the entire A-180 structural gene, massively expressed under the control of the tac promoter after lactose induction. In contrast to the mutated completed amylase, however, the product which is formed is now exported into the periplasm or the culture supernatant or suitable *E. coli* strains. The exported protein is stable, that is to say it is not degraded, and its enzymic properties are identical in terms of product specificity with those of the complete amylase A-180.

Hence, this gene product meets all the requirements necessary for the production of G5.

Example 6: Expression and Secretion of the Amylase A-180 and of the A-180 Derivative (A-180D) in Various *E. coli* Strains The *E. coli* strains HB101 and WCM100 are used for expression of the amylase A-180 or of the G5-specific 63 kDa A-180 derivative A-180D. HB101 is deposited at the Deutsche Sammlung von Mikroorganismen (DSM 1007), and WCM100 can be obtained by the process described in European Patent Application No. 338,410. It can be replaced for the expression and secretion of the amylases by other strains obtainable by the process disclosed in European Patent Application No. 338,410. The *E. coli* strains contain the expression plasmid pEX1051 for the expression of A-180, and the expression and secretion plasmid pEX21 for the expression of A-180D. 1,000 ml of nutrient medium (10 g/l peptone from casein, 5 g/l yeast extract, 10 g/l NaCl, 5 g/l lactose and 0.1 g/l ampicillin) are inoculated With 20 ml of a preculture of the particular strain (in the same medium) and incubated aerobically at 20° C. (pEX1051) or 25° C. (pEX21). After 48 hours (pEX1051) or 24 hours (pEX21), the cells are harvested by centrifugation of the culture broth.

When the strains HB101/pEX1051 and WCM100/pEX1051 are used, the harvested cells are washed with TC buffer, suspended in 1/200 of the culture volume of TC buffer and lyzed using ultrasound (Sonifier) or pressure (French press). The resulting cell lysates are treated with DNase and then centrifuged at 10,000×g for 10 minutes. After this centrifugation the supernatant (which will hereinafter be referred to as "cytoplasmic fraction") contains the amylase A-180 and can be used directly for starch conversion.

When strain HP101/pEX21 is used, the amylase A-180D, which is located in the periplasm, is extracted from the cells by CHCl$_3$ treatment (Ames et al (1984) J. Bact., 160; 1181–1183). For this, the spun-down cells are suspended in 5 ml of 10 mM Tris/HCl, pH 8.0, mixed with 5 ml of CHCl$_3$ and incubated at room temperature for 15 minutes. The suspension is then diluted with 40 ml of TC buffer and centrifuged at 6,000×g for 20 minutes. After centrifugation, the cell pellet is discarded. The supernatant (periplasmic fraction) contains 60% to 70% of the amylase A-180D formed. Other proteins contained in the plasmic fraction do not inhibit the A-180D activity so that further purification is not necessary.

When strain WCM100/pEX21 is used, the harvested cells are discarded. Under the described conditions, the culture supernatant contains 0.1–0.5 g of the recombinant gene product A-180D, while the inducer lactose has been almost completely consumed by this time. The cell-free culture supernatant can be used directly for starch conversion.

Example 7: Starch Conversion With Maltopentaose Producing Amylases Obtained From Isolate 163-26 or *E. coli*

Example 7.1: Starch Conversion With Amylase A-180 Purified From the Culture Supernatant From Isolate 163-26

Purified amylase A-180 is dissolved to a concentration of 50 μg/ml in TC buffer. A 10% solution of soluble starch in TC buffer is brought to a temperature of 45° C. The two solutions are mixed in the ratio 1:1 and incubated at 45° C. After 1 hour, the reaction is stopped by adding 1.5 parts by volume of methanol. The unhydrolyzed residual starch precipitated by the methanol addition is spun down. The hydrolysis products remaining in the solution can be qualitatively and quantitatively investigated by reversed phase column chromatography. In a typical starch conversion in which 1 ml of enzyme solution and 1 ml of substrate solution have been employed, 18.5% of the starch contained in the mixture was hydrolyzed after 1 hour. The resulting products have the following composition: G5, 82.7%; G4, 6.4%; G3, 4.2%; G2, 3.9%; G1, 2.8%.

Example 7.2 Starch Conversion With Amylase A-180 Contained in the Cytoplasmic Protein Fractions From *E. coli* Cells The cytoplasmic protein fractions from *E. coli* HB101/pEX1051 or *E. coli* WCM100/pEX1051 are prepared as described in Example 6. The concentration of the proteins is adjusted to 2 mg/ml with TC buffer. 35 ml of a 30% Noredux 150B solution (in TC buffer) are equilibrated at 45° C. Noredux 150B is a starch partially hydrolyzed by acid treatment and supplied by Henkel. The substrate is then mixed with 5 ml of the protein solution (2 mg/ml) and incubated at 45° C. 4 ml samples of the mixture are removed after 1, 2, 3 and 4 hours and mixed with 6 ml methanol and are centrifuged. The qualitative and quantitative composition of the soluble products in each supernatant is determined by HPLC analysis. The results a typical starch conversion with amylase A-180 contained in the cytoplasmic protein fraction of *E. coli* HB101/pEX1051 or *E. coli* WCM100/pEX1051 are shown in the following table:

|  | 1 h | 2 h | 3 h | 4 h |
|---|---|---|---|---|
| Proportion of Substrate Hydrolyzed | 12.1% | 19.9% | 24.95% | 31.1% |
| Product Composition: | | | | |
| Maltopentaose: | 100% | 79% | 72% | 64% |
| Maltotetraose: | 0% | 8.5% | 10.4% | 12.2% |
| Maltotriose: | 0% | 7.5% | 10.4% | 11.6% |
| Maltose: | 0% | 5% | 6.2% | 7.4% |
| Glucose: | 0% | 0% | 1% | 4.8% |

95 ml of 10% Noredux 150B solution are equilibrated at 45° C. The solution is then mixed with 5 ml of periplasmic fraction of *E. coli* HB101/pEX21 (compare Example 6) and incubated at 45° C. After 1 hour, the reaction is stopped by adding 150 ml of methanol. The mixture is centrifuged; the product composition in the supernatant is then determined by HPLC analysis. Under the conditions described, 38.4% of the employed substrate is hydrolyzed after 1 hour. The resulting products have the following composition: G5, 67.7%; G4, 11.1%; G3, 1.7%; G2, 8.7%; G1, 10.8%.

Example 7.4: Starch Conversion With Amylase A-180D Contained in the Culture Supernatant From *E. coli* WCM100/pEX21

75 ml of 10% Noredux 150B solution are equilibrated at 45° C. The solution is then mixed with 25 ml of culture supernatant from *E. coli* WCM100/pEX21 (compare Example 6) and incubated at 45° C. After 1 hour, the reaction is stopped by adding 150 ml of methanol. The mixture is centrifuged; the product composition in the supernatant is then determined by HPLC analysis.

After one hour, there was 15.8% composition of the substrate employed. The product composition was:

| | |
|---|---|
| Maltopentaose: | 91.3% |
| Maltotetraose: | 5.4% |
| Maltotriose: | 1.2% |
| Maltose: | 0.9% |
| Glucose: | 0.9% |

While only two embodiments of the present invention have been shown and described, it is to be understood that many changes and modifications may be made thereunto without departing from the spirit and scope of the invention as defined in the appended claims.

---

What is claimed is:

1. A biologically pure culture of alkalophilic bacteria having all of the identifying properties of isolate 163-26 having the accession number DSM 5853.

* * * * *